United States Patent [19]

Vance

[11] Patent Number: 5,511,559
[45] Date of Patent: Apr. 30, 1996

[54] EXCHANGEABLE GUIDEWIRE

[75] Inventor: Jeffrey D. Vance, Hugo, Minn.

[73] Assignee: Schneider (USA) Inc., Plymouth, Minn.

[21] Appl. No.: 346,628

[22] Filed: Nov. 30, 1994

Related U.S. Application Data

[62] Division of Ser. No. 61,083, May 14, 1993, Pat. No. 5,404,886.

[51] Int. Cl.$^6$ ....................................................... A61B 5/00
[52] U.S. Cl. ............................................................... 128/772
[58] Field of Search ................................... 128/657, 658, 128/772; 604/95, 164, 280–283

[56] References Cited

U.S. PATENT DOCUMENTS

| | | | |
|---|---|---|---|
| 4,827,941 | 5/1989 | Taylor et al. | 128/657 |
| 4,846,193 | 7/1989 | Tremulis et al. | 128/772 |
| 4,875,489 | 10/1989 | Messner et al. | 128/772 |
| 4,907,332 | 3/1990 | Christian et al. | 128/657 |
| 4,917,103 | 4/1990 | Gambale et al. | 128/772 |
| 4,922,923 | 5/1990 | Gambale et al. | 128/772 |
| 4,958,642 | 9/1990 | Christian et al. | 128/772 |
| 4,966,163 | 10/1990 | Kraus et al. | 128/772 |
| 4,969,879 | 11/1990 | Lichte | 604/283 |
| 5,031,636 | 7/1991 | Gambale et al. | 128/772 |
| 5,109,867 | 5/1992 | Twyford, Jr. | 128/772 |
| 5,113,872 | 5/1992 | Jahrmarkt et al. | 128/772 |
| 5,117,838 | 6/1992 | Palmer et al. | 128/772 |
| 5,133,364 | 7/1992 | Palermo et al. | 128/772 |
| 5,188,621 | 2/1993 | Samson | 128/772 |
| 5,195,535 | 3/1993 | Shank | 128/772 |
| 5,197,486 | 3/1993 | Frassica | 128/772 |
| 5,234,002 | 8/1993 | Chan | 128/772 |
| 5,247,942 | 9/1993 | Prather et al. | 128/772 |

OTHER PUBLICATIONS

Article entitled "Guide Wire Extension" by Constantin Cope, M.D., p. 263 form *Radiology*, vol. 157, No. 1 1985.

*Primary Examiner*—Max Hindenburg
*Attorney, Agent, or Firm*—Haugen and Nikolai

[57] ABSTRACT

A guidewire for guiding and exchanging body insertable catheters includes a body insertable guide section and an exchange section, both formed of flexible wire. In one embodiment, a pin connector at the distal end of the exchange section includes a truncated conical head, a shank, and a groove between the head and the shank. A socket connector is attached to the proximal end of the guide section. Four indentations are formed in the socket connector, spaced apart angularly 90° from one another. The maximum diameter of the conical head is greater than the distance between opposed nodules. As, the pin connector is insertable into the socket, it temporarily elastically deforms the socket as the head moves past the nodules. The nodules become captured within the groove, to allow rotation of the exchange section relative to the guide section while preventing any substantial axial relative movement of the sections. The exchange section can be disconnected from the guide section by withdrawing the pin connector proximally, again elastically deforming the socket as the head passes the nodules. The connectors permit repeated connections and disconnections, so the guidewire sections are reusable. In another embodiment, the pin connector has a cylindrical head and a narrower recess adjacent the head, and an indentation is formed in the socket connector with a gradually inclined wall that terminates in a steeply inclined edge.

40 Claims, 3 Drawing Sheets

EXCHANGEABLE GUIDEWIRE

This is a Divisional of copending application Ser. No. 08/061,083, filed on May 14, 1993.

BACKGROUND OF THE INVENTION

The present invention relates to devices employed in catheter guiding and exchanging procedures, and more particularly to guidewire and exchange wire interconnection apparatus.

Cathetertzation procedures, e.g. percutaneous transluminal angioplasty catheterization (PCTA), involve insertion of catheters into blood vessels and other body passageways. Frequently such passageways are convoluted, giving rise to difficulties in inserting the catheters. Accordingly, guidewires are employed to insure accurate positioning of body-inserted catheters.

More particularly, a guidewire is inserted and maneuvered along arterial or other passageways to the desired treatment site, leaving a proximal portion of the guidewire outside of the patient. Next, the catheter is threaded onto the guidewire proximal portion, which is received into a lumen formed in the catheter. The catheter is advanced over the guidewire, and thus guided to the desired treatment site. Typically the guidewire is at least slightly longer than the catheter, so that when the catheter is completely advanced to the treatment site, at least part of the guidewire proximal end portion protrudes from the catheter. For example, for a catheter length of 130 centimeters, the guidewire length can be about 150 centimeters.

Frequently in catheterization, the need arises to exchange catheters. Preferably the exchange is accomplished with the guidewire remaining, in place, to avoid tile need to maneuver yet another guidewire to tile treatment site. An exchange requires gripping the guidewire proxtmal end portion to maintain its position while the catheter is removed in the proximal direction. However, well before the originally inserted catheter can be withdrawn in this manner, it completely covers the guidewire, and the physician or other user can not simultaneously maintain the guidewire and proximally move the catheter.

In view of this difficulty, the usual approach has been to remove the guidewire from the patient, leaving the originally inserted catheter in place to guide the advancement of an exchange wire to the treatment site. The exchange wire is substantially longer than the guidewire. The proximal portion of the exchange wire, remaining outside of the patient after complete insertion, is longer than the length of the catheter. Thus, the exchange wire can be maintained while the catheter is completely withdrawn from the patient. After a replacement catheter is inserted over the exchange wire, the exchange wire is removed and the guidewire reinserted.

The repeated advancing and withdrawing of guidewires and exchange wires presents undue risk of trauma to the blood vessels or other lumens, and increases the complexity and required time for the catheterization procedure.

Several guidewire and exchange wire coupling schemes have been proposed to avoid the need for the wire exchanges. For example, U.S. Pat. No. 4,917,103 (Gambale et al) and U.S. Pat. No. 4,922,923 (Gambale et al) disclose a guidewire and exchange wire interconnection system. A hollow tubular fitting is provided at the proximal end of the guidewire, while a reduced diameter tip is formed at the distal end of the exchange wire. With the distal tip inserted into the tube, the tube is crimped to form a permanent coupling of the wires.

U.S. Pat. No. 4,966,163 (Kraus et al) shows an extendable guidewire including a main section and an extension section. A releasable coupling of these sections is provided by an externally threaded male contact at the proximal end of the main section, and an internally threaded female contact at the distal end of the extension section. The female contact is mounted to rotate relative to the extension section.

Yet another coupling scheme is disclosed in U.S. Pat. No. 4,827,941 (Taylor et al). A guidewire assembly includes a main section with a reduced diameter undulating (sinusoidal) male contact at its proximal end. An extension section includes a tube at its distal end. The sinusoidal contact elastically deforms as it is inserted into the tube, to provide a friction fit.. A similar approach is shown in U.S. Pat. No. 4,958,642 (Christian et al). Another friction fit approach is disclosed in U.S. Pat. No. 4,875,489 (Messner et al). A main section of an extendable guidewire has a tapered proximal end. An auxiliary section of the guidewire has a tube at its distal end. The tube has a longitudinal gap, and thus expands to receive the tapered end of the main section and resiliently retain the tapered end once inserted.

While the above approaches perhaps are an improvement as compared to multiple wire exchanges, each encounters difficulties, particularly in connection with smaller guidewires and exchange wires, which can have diameters as low as ten one-thousandths of an inch.

Therefore, it is an object of the present invention to provide a single device for performing the functions of the guidewire and the exchange wire in catheterization procedures.

Another object of the invention is to provide a simple and reliable means for releasably coupling a guidewire and an exchange section proximal to the guidewire.

A further object is to provide a guidewire/exchange wire system with separate guide and exchange sections releasably coupled to one another in a manner that prevents the transfer of torque from one section to the other.

Yet another object is to provide a guidewire with complementary contacts for coupling an exchange section to a guide section of the guidewire, in a manner that affords a tactile sense of completing the connection.

SUMMARY OF THE INVENTION

To achieve these and other objects, there is provided an interconnection apparatus for body insertable guidewires and exchange wires. The apparatus includes a first connector fixed to one end of a first wire. The first connector is substantially symmetrical about 1a first connector axis and has first and second axially opposite end regions. A groove is formed in the first connector between the end regions. A second connector, fixed to one end of a second wire, has a second connector axis and a projection means. The first and second connectors are positionable in confronting and axially aligned relation, for axial movement of the connectors relative to one another toward a mechanical coupling. When the connectors are mechanically coupled, the projection means extends radially into the groove. At least one of the connectors is elastically deformable to allow passage of the projection means axially inward past one of the end regions and into the groove as the connectors are moved axially relative to one another. Once the projection means has passed that end region and resides within the groove, the end regions tend to confine the projection means within the groove to prevent any substantial axial movement of the connectors relative to one another away from the mechanical coupling.

Preferably the first and second connectors, when mechanically coupled, are rotatable relative to one another about the first connector axis. This prevents the transfer of torque from one of the wires to the other, and thus reduces or eliminates torsional stress that otherwise can lead to kinking or damage, particularly for wire sections of small diameter, e.g. ten mils.

To achieve a releasable coupling, the flexible connector further is elastically deformable to allow axially outward passage of the projection means away from the groove and past the first end region of the first connector, thus to disengage the first and second wires.

In one preferred version of the interconnection apparatus, the first end region is a truncated cone that diverges in the axial direction toward the groove, and the second end region is a shank on the opposite side of the groove from the cone. The outside diameter of the shank and the maximum outside diameter of the truncated cone are substantially equal, both being greater than the outside diameter of the groove. The complementary second connector is a socket having an annular wall, with the projection means comprising four indentations formed in the annular wall along a medial region of the socket. The indentations are angularly spaced apart from one another by 90°, to form two pairs of opposed dimples or nodules at the medial region of the socket. The diameter of the truncated cone and shank is greater than the distance between each pair of nodules. Consequently the socket yields along its medial region to allow passage of the truncated cone, to position the nodules within the groove. Once the truncated cone is past the nodules, they are captured within the groove. The truncated cone and shank cooperate to maintain the nodules in the groove, and thereby maintain the mechanical coupling of the connectors.

The outside diameter of the groove can be selected with reference to the distance between opposed nodules, to permit a substantially free rotation of the socket relative to the first connector. This prevents any substantial transmission of torque from one of the wires to the other.

In practice, the first connector (a distal pin) is formed into the exchange wire at its distal end, with the socket fixed to the proximal end of the guidewire. With the guidewire inserted into the patient and with its distal tip at the treatment site, the proximal end portion of the guidewire, including the socket, remains outside of the patient. The exchange section of wire is coupled to the guidewire by sliding the first connector distally into the socket, until the projecting nodules and groove are axially aligned.

As mentioned, some elastic deformation of the socket is required to permit the projections to clear the truncated cone clearance of the cone leads to at least partial return of the socket to its normal, unstressed configuration, which gives the user a tactile sensation of the mechanical coupling.

Thus, the combination of the pin connector and socket connector provide for a reliable, releasable, and repeatable mechanical coupling of guidewire and exchange sections. The coupling is achieved by simple relative sliding of the pin connector and socket connector, and entry of the protrusions into the groove signals a physician or other user that the coupling is accomplished. The same type of motion, i.e. relative sliding of the connectors, disengages the mechanical coupling. Thus, connecting and disconnecting the wire sections demands relatively little attention on the part of the physician, who then is able to devote most of his or her attention to the catheterization procedure at hand.

IN THE DRAWINGS

For a further understanding of the above and other features and advantages, reference is made to the following detailed description and to the drawings, in which.

DETAILED DESCRIPTION OF THE PREFERRED EMBODIMENT

Figure 1:
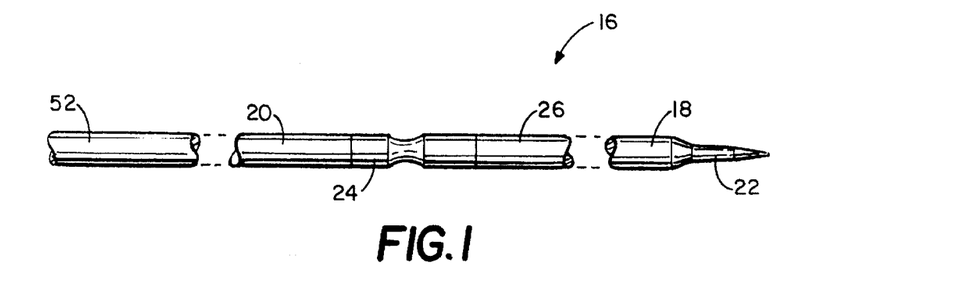
FIG. 1 is a side elevation of a guidewire assembly including connected guide and exchange sections constructed in accordance with the present invention.

Turning now to the drawings, there is shown in FIG. 1 an exchangeable guidewire 16. The guidewire includes two releasably coupled sections: a guide section 18 and an exchange section 20. Sections 18 and 20 preferably are constructed of stainless steel, for example a type of steel known as "No. 304" stainless steel, each being approximately 150 centimeters in length. Guide section 18 and exchange section 20 have the same diameter, which preferably is in the range of from about 0.010 inches to about 0.060 inches. Guide section 18 has a distally converging distal tip 22, and a socket connector or sleeve 24 at its proximal end. Exchange section 20 has a proximal end and a distal end removably inserted into socket 24.

Figure 2:
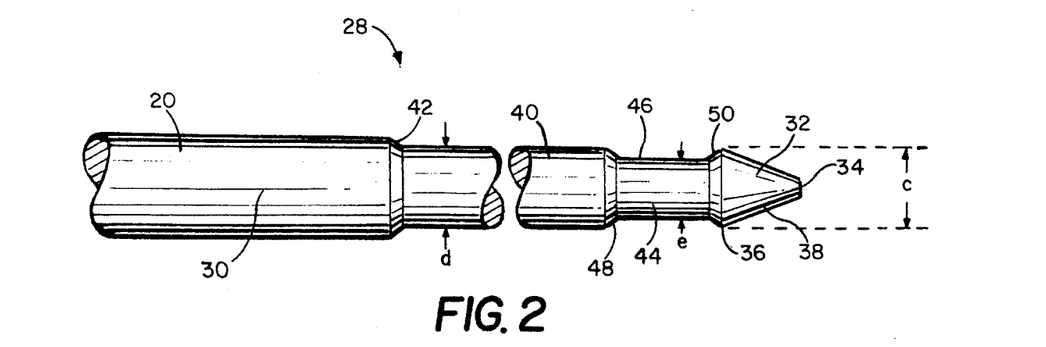
FIG. 2 is an enlarged side elevation of a distal end region of the exchange section.

The distal end region of exchange section 20 is shown in FIG. 2. A portion of the stainless steel wire at the distal end is selectively removed, to form a pin connector 28. More particularly, material is removed by a precision grinding of the exchange section by relative rotation of the exchange section and a grinding tool (not shown) about a central longitudinal axis 30 of the exchange section. As a result, pin connector 28 is concentric on axis 30, and transverse profiles, i.e. profiles taken perpendicular to axis 30 along the connector, are circular.

Pin connector 28 has a distal tip or head 32 in the form of a truncated cone, diverging in the proximal direction from a blunt distal end 34 to a maximum cone diameter at 36. This divergence is gradual, in the sense that the angle between the inclined cone surface 38 and axis 30 is less than 45°, and more preferably about 20°. Connector 28 further includes a proximal shank 40, having an outside diameter substantially equal to the maximum diameter of cone 32. Between shank 40 and the remainder of exchange section 20 is an inclined surface 42.

Pin connector 28 further includes an annular recess or groove 44, formed along an intermediate region of the connector between shank 40 and cone 32. Over most of its length, groove 44 has an annular surface 46 concentric on axis 30. On opposite sides of surface 46 are inclined groove surfaces 48 and 50 near the shank and cone, respectively. Surfaces 48 and 50 are steeply inclined, in the sense that the angle of each surface with respect to axis 30 is at least 45°.

Figure 3:
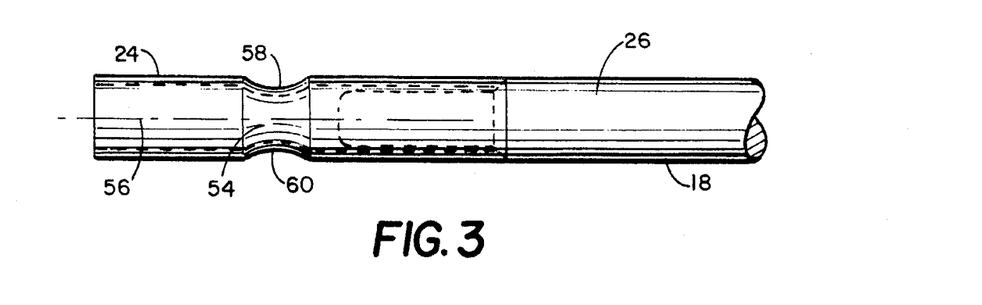
FIG. 3 is an enlarged side elevation of a proximal end region of the guide section.
Figure 4:
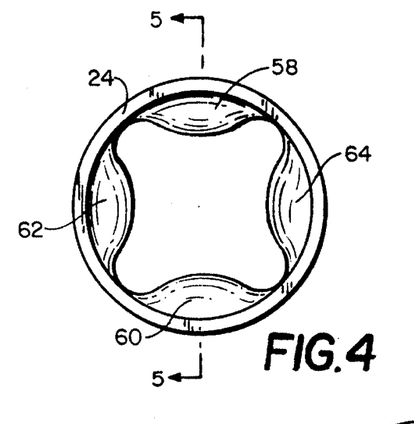
FIG. 4 is a proximal end view of the guide section.

FIG. 3 shows the proximal end region of guide section 18, including socket connector 24 and a proximal end of the wire forming the guide section. Socket connector 24, over most of its length, has an annular wall in the form of a hollow, circular cylinder. However, at its medial region 54, socket connector 24 is formed to provide four indentations projected inwardly toward a longitudinal central axis 56 of the socket connector. These indentations provide nodules or dimples, formed angularly spaced apart from one another at 90° intervals. Thus, there are two opposed pairs of the nodules, one including nodules 58 and 60, and the other pair including nodules 62 and 64 (FIG. 4).

Figure 5:
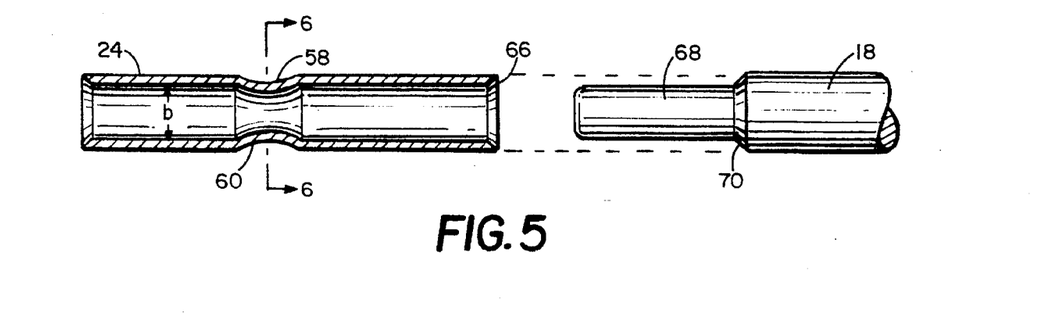
FIG. 5 is a sectional view taken along the line 5—5 in FIG. 4, with a socket connector of the guide section shown removed from the remainder of the guide section.
Figure 6:
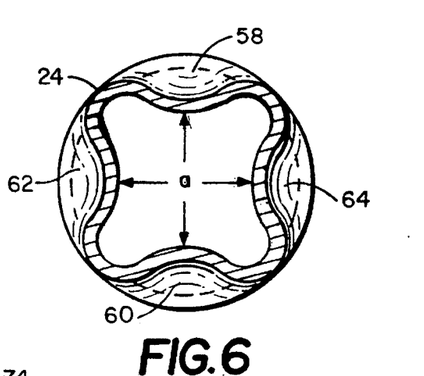
FIG. 6 is a sectional view taken along the line 6—6 in FIG. 5.

As perhaps best seen in FIG. 5, the distance "a" between the pair of indentations 58 and 60 is less than the nominal inside diameter "b" of socket connector 24 over the majority of its length. The same is true for the distance between indentations 62 and 64. At the distal end of the socket connector is an annular beveled surface 66.

Further in FIG. 5, the proximal end of the guide section is withdrawn from the socket connector to reveal a proximal extension 68 having an outside diameter approximately equal to but slightly less than inside diameter "b" of the socket connector. Between extension 68 and the remainder of guide section 18 is an annular beveled transition surface 70. Socket connector 24 is permanently secured to guide section 18, by an interference fit of extension 68 within socket connector 24, with parallel beveled surfaces 66 and 70 contiguous. Preferably an adhesive is applied to at least one of surfaces 66 and 70 before the socket connector and guide section are engaged, in which case the adhesive further secures the connection.

The maximum cone diameter and the shank outer diameter, indicated respectively at "c" and "d" in FIG. 2, are approximately equal to one another, greater than distance "a" between indentations 58–64, and less than inside diameter "b" of socket connector 24. An outside diameter of groove 44, indicated at "e" in FIG. 2, likewise is less than diameters "c" and "d", and preferably is about equal to distance "a".

Figure 7:
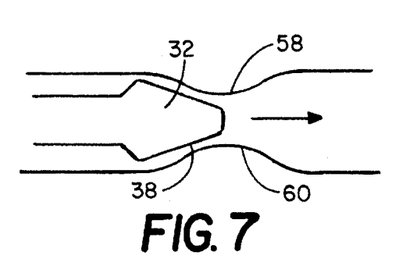
FIGS. 7–9 are diagrammatic views illustrating progressive insertion of a pin connector of the exchange section into the socket.
Figure 8:
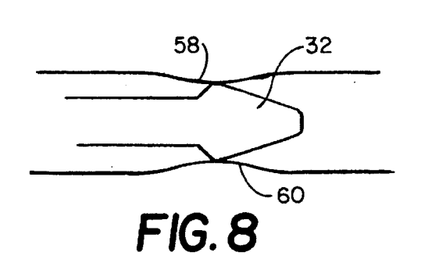
Figure 9:
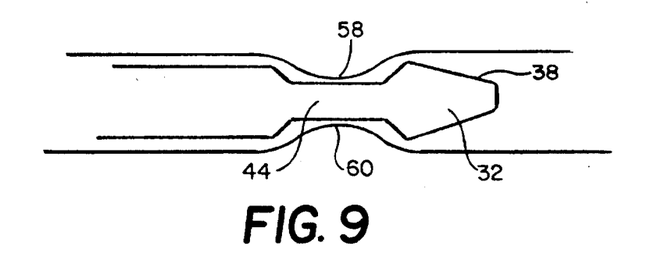

Pin connector 28 and socket connector 24 provide for a releasable mechanical coupling of the exchange and guide sections, in which the socket connector surrounds the pin connector, indentations 58, 60, 62 and 64 are aligned with and captured within groove 44, and axes 30 and 56 substantially coincide. The joinder of connectors 24 and 28 is illustrated in FIGS. 7–9. As seen in FIG. 7, conical head 32 of the pin connector is inserted into the proximal end of socket connector 24, then moved distally toward indentations 58–62. This insertion is facilitated by the fact that the cone diameter, near distal end 34, is substantially less than the distance "a" between opposed indentations, and thus is substantially less than the interior diameter "b" of the socket connector.

As pin connector 28 is moved rightward as viewed in FIGS. 7–9, cone 32 eventually encounters the indentations. Further rightward movement of the cone elastically deforms socket connector 24 particularly along medial region 54. Thus, surface 38 of cone 32 functions as a cam, forcing indentations 58–64 apart from one another against the elastic restoring force of the socket, until the maximum diameter portion of the cone is axially aligned with the indentations, as viewed in FIG. 8. The gradual (20) incline of cone surface 38 facilitates insertion of connector 28. More particularly, due to the gradual incline, the required axial insertion force is relatively small as compared to the radial force required to elastically deform the socket connector.

When pin connector 28 is inserted beyond the position illustrated in FIG. 8, indentations 58–64 move radially inward due to the elastic restoring force of the socket, into an engagement with groove surface 46. This movement is relatively rapid, due to the steep incline of groove surface 50 and the restoring force. The rapid movement and engagement provide a tactile sensation to the physician or other user attempting to connect the extension and guide sections, that a mechanical coupling has been achieved.

As shown in FIG. 9, when connectors 24 and 28 are coupled, indentations 58–64 are axially aligned with and captured within groove 44. The relatively steep incline of beveled surface 50 insures that a proximal removal of pin connector 28 requires a substantially greater axial force as compared to connector insertion. The steep incline of beveled surface 48 likewise resists distal insertion of pin connector 28 beyond the desired axial alignment.

Accordingly, the mechanical coupling does not depend upon a frictional engagement of the nodules or indentations against the groove surface. There is no need for an elastic restoring force to maintain the nodules against the groove surface. In fact, in the preferred mechanical coupling, the distance "a" between indentations is approximately equal to the groove diameter "e" so that pin connector 28, when mechanically coupled within socket connector 24, remains free to rotate relative to the socket about connector axes 30 and 56. Consequently, exchange section 20 is maintained axially relative to guide section 18 when coupled, yet is free to rotate relative to the guide section. This arrangement prevents any substantial transfer of torque from the exchange section to the guide section, and thus substantially eliminates the chance for twisting, kinking, and other damage to the wires forming the guide and exchange sections. This advantage is increasingly critical for wire sections having small diameters, i.e. at or approaching 0.010 inch.

As previously mentioned, the mechanical coupling of connectors 24 and 28 is releasable. More particularly, exchange section 20 is pulled proximally relative to the guide section, whereby inclined surface 50 of the groove acts as a cam to deform the socket connector and thereby move the indentations radially outward and apart from one another. While the required axial force for disconnecting the extension section is greater than the insertion force in joining the sections, disconnection nonetheless is conveniently accomplished manually, with one hand gripping each of the extension and guide sections. Regardless of whether pin connector 28 is being inserted or removed, the requisite deformation of socket connector 24 is elastic, which allows for repeated connections and disconnections as required during the medical procedure, without reducing the efficacy of the mechanical coupling.

The use of guidewire 16 can be considered in connection with an angioplasty procedure to treat a blood vessel occlusion, formed for example due to an accumulation of plaque. This exemplary procedure involves two dilatation steps, followed by placement of a prosthesis.

The procedure is initiated by percutaneous and intravascular insertion of guide section 18, to a point where distal tip 22 is aligned with the occlusion site. At this stage, guide section 18 is free of exchange section 20. Nonetheless, guide section 18 is sufficiently long (e.g. 150 centimeters) such that with distal tip 22 so aligned, a proximal portion of the guide section including socket connector 24 remains outside of the patient.

Next, an initial dilatation catheter (not shown) is inserted, by placing its distal end over proximal end 52 of guide section 18. A lumen in the dilatation catheter accepts the guide section. The dilatation catheter is progressively advanced until a balloon at the distal end of a dilatation catheter is aligned with the occlusion. With guide section 18 in place, the dilatation catheter is positively directed toward the treatment site, and thus can be inserted relatively quickly without requiring undue attention. A proximal portion of the dilatation catheter remains outside of the patient, and the proximal portion of the guide section extends at least a slight distance proximally of the dilatation catheter. At this stage, the dilatation balloon is expanded to enlarge the vessel at the treatment site.

After the initial expansion of the vessel at the occlusion, the dilatation catheter is withdrawn. The conventional procedure involved removing a guidewire and inserting a much longer exchange wire. In accordance with the present invention, guide section 18 remains in place, while exchange section 20 is coupled to the guide section by inserting pin connector 28 into socket connector 24, while holding the socket connector in place to maintain the axial position of guide section 18. A simple and direct axial (distal) pushing of the pin connector is all that is required. The socket connector is elastically deformed temporarily, then rapidly returns to its normal configuration as groove 44 becomes aligned with indentations 58–64. This return of the socket connector brings the indentations against groove surface 46, providing a "snap fit" sensation that positively informs the physician with a tactile sensation of a successful coupling.

Several advantages arise from the fact that socket connector 24, when coupled, is in a relaxed state, rather than elastically deformed. First, there is no risk that gradually diminishing elastic restoring force might degrade the connection. Secondly, no torque is transferred through the interconnection. Accordingly, exchange section 20 can be rotated (whether intentionally or inadvertently) without rotating the proximal end of the guide section. Thus the exchange section can be manipulated as necessary, without the risk of twisting or kinking along the guide section.

Returning to the procedure, the coupling of guide section 18 and exchange section 20 substantially increases the length of wire outside of the patient (e.g. by another 150 centimeters). Exchange section 20 can be gripped by hand to maintain the axial position of guide section 18 while the initial dilatation catheter is proximally withdrawn.

After withdrawal, the guide and exchange sections remain coupled, as a second dilatation catheter (not shown) is inserted. More particularly, the second dilatation catheter has a lumen that accepts proximal end 26 of exchange section 20, enabling progressive advancement of the dilatation catheter along the guidewire until the second (perhaps larger) dilatation balloon is aligned at the treatment site. At this stage, connectors 24 and 28 are proximal of the second dilatation catheter, and it is advantageous to disconnect and remove the exchange section. Disconnection is accomplished easily by hand, holding socket connector 24 in place while proximally pulling the exchange section near pin connector 28. Disconnection requires temporary elastic deformation of socket connector 24. Disconnection is easily accomplished by hand. With the exchange section removed, there is no need for an attendant to handle an unwieldy length of exchange wire, and the physician can concentrate on the angioplasty procedure at hand, without distraction due to the exchange wire, as the second dilatation balloon is expanded against the occlusion.

After the second dilatation step, exchange section 20 is again coupled to guide section 18 as described above, and the second dilatation catheter is withdrawn over the guide and exchange sections. With the sections remaining coupled, a prosthesis delivery catheter is inserted over the proximal end of the exchange section, and advanced progressively until a prosthesis (e.g. a radially self-expanding stent) at the distal end of the catheter is aligned at the treatment site. At this point the exchange section is disconnected and removed, leaving just the proximal portion of the guide section exposed beyond the prosthesis delivery catheter. The physician can concentrate on prosthesis deployment and delivery, free of concern about exchange section 20.

Following prosthesis deployment, guide section 18 and the deployment catheter are withdrawn. Alternatively, should any further catheters be required (e.g. an endoscopic catheter to view stent placement), the guide and exchange sections are coupled once again to enable withdrawal of the delivery catheter while guide section 18 remains in place. In either event, repeated connections and disconnections of the guide and exchange sections do not structurally alter either connector, or in any other manner degrade the quality of the mechanical coupling.

Figure 10:
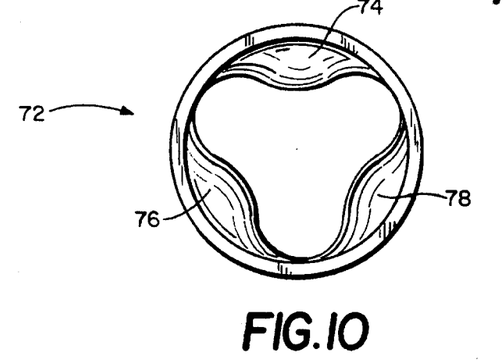
FIG. 10 is an end view of an alternative embodiment socket connector.

FIG. 10 shows a socket connector 72 utilized in an alternative guidewire system, in which the exchange section is similar to exchange section 20. Three indentations 74, 76 and 78 are formed in the annular wall of socket 72 at its medial region, with the indentations spaced apart from one another angularly by about 120°. Insertion of the exchange section into socket 72 forces indentations 74–78 radially outward away from one another, much in the manner as described above in connection with socket connector 24. Again, mechanical coupling involves an axial alignment of the indentations with a groove in the tip connector, with the indentations captured within the groove.

FIGS. 11–15 illustrate another highly preferred embodiment guidewire 80, including a guide section 82 and an exchange section 84, coupled relative to one another by a socket connector 86. More particularly, a pin connector 88 at the proximal end of the guide section, and a pin connector 90 at the distal end of the exchange section, are inserted into socket connector 86, to be retained within the socket connector as shown in broken lines.

Figure 12:
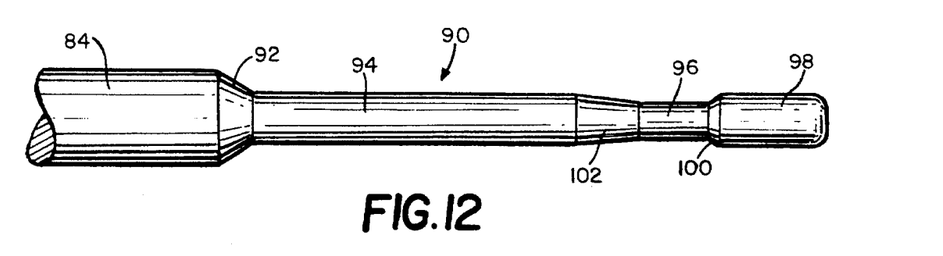

FIG. 12 shows pin connector 90 in greater detail. A truncated conical region 92 converges distally from the nominal diameter of the exchange section to a shank 94 of the pin connector. An annular recess or groove 96 is formed in the pin connector, near a cylindrical head 98 that forms the distal end of the pin connector. A steeply inclined groove surface 100 is disposed between the groove and the head. Between the groove and shank 94 is a more gradually inclined groove surface 102.

Pin connector 88 of the guide section is substantially identical to pin connector 90.

Figures 13, 14, 15:
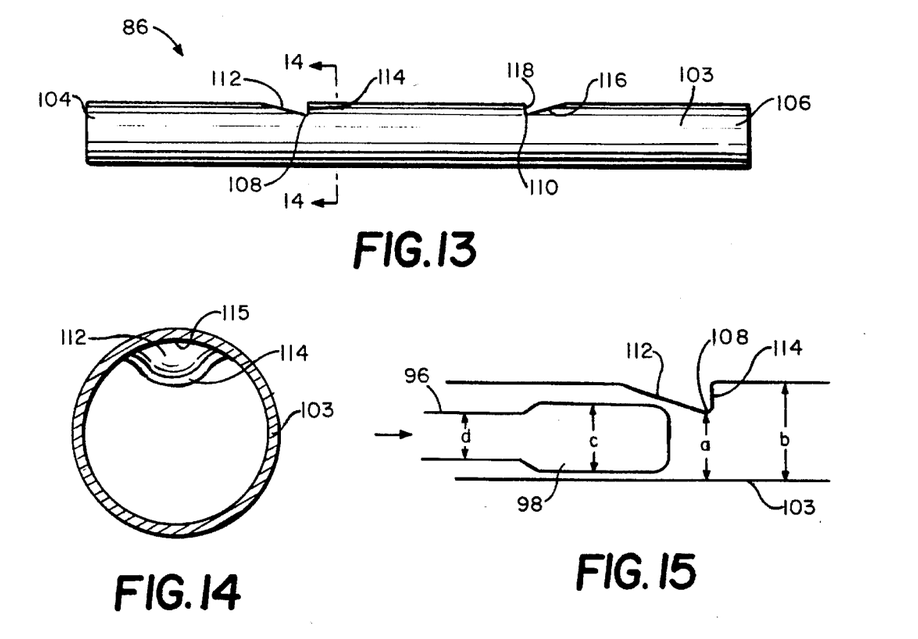

Socket connector 86 is shown in greater detail in FIGS. 13 and 14. The socket includes an annular wall 103 with opposite proximal and distal ends 104 and 106 for insertion of pin connectors 90 and 88, respectively. Connector wall 103 is selectively cut and crimped to form a proximal indentation 108 and a distal indentation 110, facing in opposite directions but otherwise substantially identical to one another. In each case, a transverse slit through connector wall 103 permits a controlled bending or crimping of a selected area of connector wall 103 on one side of the slit.

As seen in connection with proximal indentation 108 (FIG. 14), the result of this selective reshaping is a gradually inclined wall portion 112 having an arcuate lateral profile terminating in a relatively steep distal edge 114. Wall portion 112 is visible in FIG. 14 through an opening 115 between edge 114 and connector wall 103, which opening is formed as a result of the slit and selective reshaping.

Distal indentation 110 is substantially identical to indentation 108, having a gradually inclined wall portion 116 that terminates at a steeply inclined edge 118 (FIG. 13).

FIG. 15 schematically represents the insertion of pin connector 90 into socket connector 86. The diameter of head 98, indicated at "c" is less than the inside diameter "b" of the socket connector, but exceeds the distance "a" between proximal indentation 108 and the opposite side of wall 103. Thus, as pin connector 90 is moved rightward as viewed in the figure, head 98 eventually contacts wall portion 112 of indentation 108. Upon further rightward movement of the pin connector, head 90 elastically deforms socket connector 86, particularly in the region of indentation 108. As head 98 moves rightwardly along gradually inclined surface 112, the socket connector is deformed a sufficient amount to permit passage of the head rightwardly beyond indentation 108, to align the indentation with groove 96. The gradual incline of wall portion 112 facilitates insertion of pin connector 90, much in the same manner that previously discussed cone surface 38 promotes insertion of pin connector 28.

Once head 98 is beyond indentation 108, socket connector 86 elastically recovers, i.e. returns to the shape of its relaxed condition, wherein the indentation and opposite portion of connector wall 103 are once again separated by the distance "a". Elastic recovery is relatively rapid, due to the steep incline of groove surface 100 and the elastic restoring force in the socket connector. Thus, as before, elastic recovery provides a tactile sensation that a mechanical coupling has been achieved. The relatively steep incline of groove surface 100, and the relatively steep incline of edge 114, insure that a proximal removal of pin connector 90 requires substantially greater axial force than connector insertion.

Preferably, the distance "a" slightly exceeds the diameter "d" of groove 96, so that when mechanically coupled, pin connector 90 and socket connector 86 nonetheless remain free to rotate relative to one another, thus to allow exchange section 84 to rotate relative to guide section 82 while being maintained axially relative to the guide section. As previously noted, this feature prevents any substantial transfer of torque from the exchange section to the guide section.

Pin connector 90 includes a gradually inclined groove surface 102 proximally of groove 96, as opposed to the relatively steep surface 48 of pin connector 28. Surface 102 is not relied upon to limit the distal movement of pin connector 90 relative to socket connector 86. Rather, such distal movement is limited by conical region 92 of pin connector, as this surface encounters proximal end 104 of the socket connector.

Figure 11:
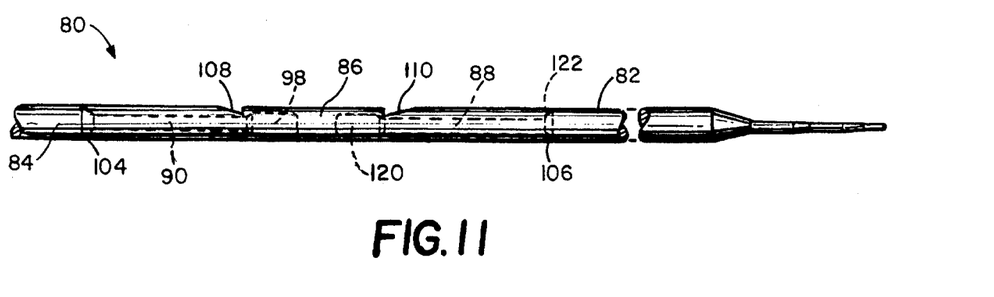
FIGS. 11–15 illustrate an alternative embodiment guidewire including pin and socket connectors.

Insertion of pin connector 88 into socket connector 86 is accomplished in much the same manner as insertion of pin connector 90, except that pin connector 88 is inserted into distal end 106 and moved in the proximal direction to the point of mechanical connection.

Thus, proximal indentation 108 and distal indentation 110 capture head 98 and a head 120 of pin connector 88, respectively, which maintains the mechanical coupling of the pin connectors within socket connector 86. Further, however, it is preferred to permanently bond the socket connector to pin connector 88 and guide section 82. This is accomplished by joining an inclined surface 122 of connector 88 to a similarly inclined surface at distal end 106 of the socket connector, after applying a suitable medical adhesive to one or both of these surfaces.

Socket connector 86 and pin connectors 88/90 afford several advantages over socket connector 24 and pin connector 28. Indentations 108/110, as compared to nodules 58–64, are easier to form, and can be formed with more consistency (tighter dimensional tolerances) over numerous repetitions. More importantly, however, is that indentations 108/110 can be formed asymmetrically, to provide the gradual wall portion in combination with the steep edge. The result, as noted above, is to facilitate insertion of the pin connectors while providing substantially increased resistance to their withdrawal, without the need for special shaping of the connector tip, e.g. as in providing conical head 32 of pin connector 28. The conical head is difficult to form, particularly for small diameter guidewires. Accordingly, elimination of the need to fabricate the cone is a substantial advantage.

Typical guidewires in accordance with the present invention can have diameters ranging from about 0.014" to 0.018" for coronary applications, and from about 0.018" to 0.063" for peripheral applications. In one preferred version of guidewire 80, the wire, pin connector and socket connector dimensions in inches are as follows:

Pin Connectors: Wire outside diameter: 0.014 Shank outside diameter: 0.009 Groove outside diameter: 0.007 Head outside diameter: 0.009

Socket Connector: Length: 0.75 Nominal inside diameter: 0.010 Distance between indentations and opposite side of socket: 1.00

Guidewire: Outside diameter: 0.014

Thus in accordance with the present invention, catheters can be exchanged repeatedly while a distal guide section remains in place for guiding each catheter to the treatment site. An exchange section is easily and quickly connected to the guide section to provide an extended proximal region of the guidewire when needed for catheter insertion or withdrawal. When no longer needed, the exchange section is easily disconnected. Because each connection and disconnection requires only a temporary elastic deformation of the connector structure, repeated connections and disconnections do not degrade the quality of the coupling. There is no substantial elastic load during coupling, further insuring against degradation and preventing the transfer of torque from the exchange section to the guide section. Finally, the manner in which the nodules of one of the connectors are captured into a groove of the other connector, provides a tactile sensation to signal the physician of a successful coupling.

What is claimed is:

1. An interconnection apparatus for body insertable guidewires and exchange wires, including:

a first connector at one end of a first wire, said first connector being substantially symmetrical about a first connector axis and having a first end region and a recessed region adjacent the first end region; and a second connector adapted for mounting at one end of a second wire, said second connector having a second connector axis and a projection means;

wherein the first and second connectors, when positioned in confronting and at least generally axially aligned relation, are movable axially toward one another into a mechanical coupling in which the projection means is aligned with and extends radially toward the recessed region; a selected one of the connectors elastically deforming to allow the first end region to travel axially inward past the projection means as the connectors are moved toward said mechanical coupling and further at least substantially elastically recovering upon movement of the connectors into said mechanical coupling; the projection means and the first end region, with the connectors in said mechanical coupling, engaging one another to limit axial movement of the connectors away from one another to maintain the mechanical coupling, wherein the first and second connectors are rotatable relative to one another when in said mechanical coupling; and wherein the selected connector further is elastically deformable, responsive to further axially outward travel of the first end region after engaging said projection means as the connectors are moved axially away from said mechanical coupling, to allow travel of the first end region axially outward past the projection means to release the mechanical coupling.

2. The apparatus of claim 1 further including:

a stop means for preventing any substantial axially inward movement of the first end region relative to the second connector, when the connectors are in said mechanical coupling.

3. The apparatus of claim 2 wherein:

the recessed region comprises a groove between the first end region and a second and opposite end region of the first connector, said projection means extending radially into the groove when the connectors are in said mechanical coupling.

4. The apparatus of claim 3 wherein:

the stop means comprises an inclined groove end surface between the groove and the second end region.

5. The apparatus of claim 2 wherein:

the stop means comprises a truncated conical surface between the first connector and the first wire and an end of the second connector, positioned to engage one another and thereby prevent further axially inward movement of the first connector relative to the second connector.

6. The apparatus of claim 3 wherein:

the first end region comprises a head, the second end region comprises a shank, and said groove has a diameter less than an outer diameter of the shank and less than an outer diameter of the head.

7. The apparatus of claim 1 wherein:

said first end region of the first connector is a truncated cone diverging in the axial direction toward the groove.

8. The apparatus of claim 7 wherein:

said second end region is a shank on the opposite side of the groove from the truncated cone, with an outside diameter of the shank and a maximum outside diameter of the truncated cone being greater than an outside diameter of the groove.

9. The apparatus of claim 8 wherein:

the outside diameter of the shank and the maximum outside diameter of the truncated cone are substantially equal.

10. The apparatus of claim 8 wherein:

said first connector, including the truncated cone, the groove and the shank, is formed by selective removal of material from said one end of the first wire.

11. The apparatus of claim 8 wherein:

said truncated cone diverges at an angle of about 20° with respect to first connector axis.

12. The apparatus of claim 11 further including:

two opposed groove end surfaces proximate the cone and the shank, respectively, said end surfaces being inclined at an angle of at least 45° relative to the first connector axis.

13. The apparatus of claim 1 wherein:

the second connector comprises a socket having an annular wall, and the first connector is inserted into the socket and surrounded by the socket when in said mechanical coupling.

14. The apparatus of claim 1 wherein:

the second connector comprises a socket having an annular wall, the first connector is inserted into the socket and surrounded by the socket when in said mechanical coupling, and the projection means comprises an indentation formed in the annular wall.

15. The apparatus of claim 14 wherein:

said indentation includes a gradually inclined wall portion that terminates in a steeply inclined edge, and wherein said first end region, when traveling axially inward toward the indentation, encounters the wall portion before encountering the edge.

16. The apparatus of claim 1 wherein:

one of the first and second connectors at least substantially surrounds the other connector when the connectors are in said mechanical coupling, to prevent substantial radial movement of the connectors relative to one another.

17. The apparatus of claim 16 wherein:

the second connector comprises a socket having an annular wall, and surrounds the first connector when the connectors are in said mechanical coupling.

18. The interconnection apparatus of claim 1 wherein:

said selected connector elastically deforms responsive to further axial travel of the first and second connectors toward one another after engagement of said first end region and projection means, as said connectors are moved toward said mechanical engagement.

19. A device for guiding and exchanging body insertable catheters, including:

a body insertable guide section formed of a flexible wire;

an exchange section formed of a flexible wire;

a first connector at an end of one of the flexible wire sections, said first connector being substantially symmetrical about a first connector axis and having a first end region and a recessed region adjacent the first end region; and a second connector at an end of the other of said flexible wire sections, said second connector having a second connector axis and a projection means;

wherein the first and second connectors, when positioned in confronting and at least generally axially aligned relation, are movable axially toward one another into a mechanical coupling in which the projection means is aligned with and extends radially toward the recessed region; a selected one of the connectors elastically deforming to allow the first end region to travel axially inward past the projection means as the connectors are moved toward said mechanical coupling and further at least substantially elastically recovering upon movement of the connectors into said mechanical coupling; the projection means and the first end region, with the connectors in said mechanical coupling, engaging one another to limit axial movement of the connectors away from one another to maintain the mechanical coupling;

and wherein said selected connector further is elastically deformable, responsive to travel of the first end region axially outward away from said mechanical coupling after engaging the projection means, to allow axially outward passage of the first end region past the projection means to release the mechanical coupling.

20. The device of claim 6 wherein:

the first end region of the first connector is a truncated cone converging in the axial direction toward the groove, and the first connector further includes a second end region comprising a shank on the opposite side of the recessed region from the truncated cone.

21. The device of claim 20 wherein:

an outside diameter of the shank and a maximum outside diameter of a truncated cone are approximately equal to one another and are greater than an outside diameter of the recessed region.

22. The apparatus of claim 6 wherein:

the first end region of the first connector comprises a cylindrical head.

23. The apparatus of claim 20 wherein:

the second connector comprises a socket having an annular wall, and the first connector is inserted into the socket and surrounded by the socket when in the mechanical coupling.

24. The device of claim 23 wherein:

the socket has a nominal inside diameter, and the projection means comprises at least one indentation formed in the annular wall.

25. The device of claim 23 wherein:

said at least one indentation includes a gradually inclined wall portion having an axially inward and steeply inclined edge.

26. The device of claim 23 wherein:

the projection means comprises four indentations formed in the annular wall along the medial region and spaced apart angularly 90° from one another to provide two pairs of opposed indentations at the medial region, wherein a distance between each pair of opposed indentations is less than the nominal inside diameter.

27. The device of claim 26 wherein:

respective outside diameters of the first end region and the second end region of the first connector, are less than the nominal inside diameter of the socket and greater than the distance between each pair of indentations.

28. The device of claim 27 wherein:

the distance between each pair of opposed indentations is at least equal to an outside diameter of the groove.

29. The device of claim 26 wherein:

the first end region of the first connector comprises a truncated cone diverging in the direction toward the groove, and the second end region of the connector comprises a shank on the opposite side of the groove from the cone and having an outside diameter substantially equal to a maximum outside diameter of the truncated cone.

30. The device of claim 21 wherein:

the guide section includes a proximal extension, and a distal end portion of the socket surrounds the proximal extension.

31. The device of claim 30 wherein:

the guide section further includes an annular beveled transition surface between the proximal extension and the remainder of the guide section, and the socket has an annular beveled distal surface parallel to the transition surface.

32. The device of claim 19 wherein:

one of the first and second connectors at least substantially surrounds the other of the connectors when the connectors are in said mechanical coupling, to prevent substantial radial movement of the connectors relative to one another.

33. The device of claim 32 wherein:

the second connector comprises a socket having an annular wall, and surrounds the first connector when the connectors are in said mechanical coupling.

34. An interconnection apparatus for body insertable guidewires and exchange wires, including:

a first connector at one end of a first wire, said first connector being substantially symmetrical about a first connector axis and having a first end region and a recessed region adjacent the first end region, said first end region having a first truncated conical surface diverging in the axial direction toward the recessed region and a second truncated conical surface between the first conical surface and the recessed region converging in the axial direction toward the recessed region; and a second connector adapted for mounting at one end of a second wire, said second connector having a second connector axis and a projection means;

wherein the first and second connectors, when positioned in confronting and at least generally axially aligned relation, are movable axially inward toward one another into a mechanical coupling in which the projection means is aligned with and extends radially toward the recessed region; said first connector engaging the projection means at the first conical surface and, upon further axially inward travel, elastically deforming the second connector to allow the first end region to travel axially inward past the projection means as the connectors are moved toward said mechanical coupling, the second connector at least substantially elastically recovering upon movement of the connectors into said mechanical coupling; the projection means and the first end region, with the connectors in said mechanical coupling, engaging one another to limit axial movement of the connectors away from one another and thus maintain the mechanical coupling;

wherein said first connector further is movable axially outward away from said mechanical coupling to cause the first end region to engage the projection means at said second conical surface and, upon further axially outward travel, elastically deforming the second connector to allow axially outward passage of the first end region past the projection means to release the mechanical coupling; and wherein the second conical surface is inclined more steeply than the first conical surface, whereby the axial force necessary to effect said further axially inward travel is less than the axial force necessary to effect said further axially outward travel.

35. An interconnection apparatus for body insertable guidewires and exchange wires, including:

a first connector at one end of a first wire, said first connector being substantially symmetrical about a first connector axis and having a first end region and a recessed region adjacent the first end region; and a second connector adapted for mounting at one end of a second wire, said second connector comprising a socket having an annular wall, said second connector further having a second connector axis and a projection means comprising at least one indentation formed in the annular wall along a medial region of the socket;

wherein the first and second connectors, when positioned in confronting and at least generally axially aligned relation, are movable axially toward one another to insert the first connector into the socket to form a mechanical coupling in which the socket surrounds the first connector and the at least one indentation is aligned with and extends radially toward the recessed region; a selected one of the connectors elastically deforming to allow the first end region to travel axially inward past the at least one indentation as the connectors are moved toward said mechanical coupling and further at least substantially elastically recovering upon movement of the connectors into said mechanical coupling; the at least one indentation and the first end region, with the connectors in said mechanical coupling, engaging one another to limit axial movement of the connectors away from one another to maintain the mechanical coupling; and wherein the selected connector further is elastically deformable, responsive to further travel of the first end region axially outward away from said mechanical coupling after engaging the at least one indentation, to allow axial travel of the first end region past said indentation to release the mechanical coupling.

36. The apparatus of claim 35 wherein:

the projection means comprises a plurality of indentations formed along the medial region and equally angularly spaced apart from one another.

37. The apparatus of claim 36 wherein:

the projection means comprises four of the indentations angularly spaced apart from one another 90 degrees to provide two pairs of opposed indentations at the medial region of the socket, wherein a distance between each pair of opposed indentations is less than a nominal interior diameter of the socket.

38. The apparatus of claim 37 wherein:

an outer diameter of the first end region of the first connector is less than the nominal interior diameter of the socket and greater than the distance between each pair of opposed indentations, and wherein the socket is elastically deformable to permit insertion of the first connector into the socket to carry the first end region past the indentations, to axially align the indentations and the groove recessed region, said recessed region being formed as a groove in the first connector.

39. The apparatus of claim 35 wherein:

an outer diameter of the second end region of the first connector is less than the nominal interior diameter of the socket and exceeds the distance between each pair of opposed indentations.

40. The apparatus of claim 39 wherein:

the distance between each pair of opposed indentations is at least equal to an outer diameter of the groove, whereby the first connector, when in the mechanical coupling, is free to rotate relative to the socket about the first connector axis.

* * * * *

UNITED STATES PATENT AND TRADEMARK OFFICE
CERTIFICATE OF CORRECTION

PATENT NO.   : 5,511,559
DATED        : April 30, 1996
INVENTOR(S)  : Jeffrey D. Vance It is certified that error appears in the above-indentified patent and that said Letters Patent is hereby corrected as shown below:

Claim 20, column 13, line 7 "6" should read -- 19 --.

Claim 22, column 13, line 18 "6" should read -- 19 --.

Claim 38, column 16, line 16 delete "groove".

Signed and Sealed this

Seventeenth Day of September, 1996

Attest:

BRUCE LEHMAN

*Attesting Officer*      *Commissioner of Patents and Trademarks*